US00PP13292P3

(12) United States Plant Patent
Olesen et al.

(10) Patent No.: US PP13,292 P3
(45) Date of Patent: Dec. 3, 2002

(54) SHRUB ROSE VARIETY 'POULBAMBE'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/776,562

(22) Filed: Feb. 1, 2001

(65) Prior Publication Data

US 2002/0152506 P1 Oct. 17, 2002

(51) Int. Cl.[7] ..... A01H 5/00

(52) U.S. Cl. ..... Plt./104

(58) Field of Search ..... Plt./104, 105

*Primary Examiner*—Bruce R. Campell
*Assistant Examiner*—Annette Para

(57) ABSTRACT

A new shrub rose shrub which has abundant, amber-yellow flowers and attractive foliage. This new and distinct variety has shown to be uniform and stable in the resulting generations from asexual propagation.

1 Drawing Sheet

CLASSIFICATION

Botanical: *Rosa hybrida* 'POULbambe'.

Commercial: Shrub rose.

SUMMARY OF THE INVENTION

The present invention constitutes a new and distinct variety of shrub rose which originated from a controlled crossing between 'POULtrav' (U.S. Plant patent application Ser. No. 09/277,240, dated Mar. 26, 1999) and 'POULurt' (described and illustrated in U.S. Plant Pat. No. 9,637 issued on Sep. 3, 1996). The two parents were crossed during the summer of 1993 and the resulting seeds were planted in a controlled environment in Fredensborg, Denmark. The new variety is named 'POULbambe'.

The new rose may be distinguished from its seed parent, 'POULtrav', by the following combination of characteristics:

1. The bloom color of 'POULbambe' is a lighter amber-yellow compared to the bloom of 'POULtrav'.

2. 'POULbambe' has smaller, more rounded flowers than 'POULtrav'.

3. 'POULbambe' is a shrub rose with an upright bushing habit, whereas 'POULtrav' is a miniature rose.

The new variety may be distinguished from its pollen parent, 'POULurt' by the following combination of characteristics:

1. 'POULbambe' has amber-yellow blooms, whereas 'POULurt' has light yellow blooms.

2. 'POULbambe' has large, double flowers, whereas 'POULurt' has smaller, semi-double flowers.

3. 'POULbambe' has more upright bushy growth habit, while 'POULurt' has lower outspreading growth habit.

The objective of the hybridization of this rose variety was to create a new and distinct variety for garden use with unique qualities, such as:

1. Uniform and abundant amber-yellow flowers;

2. Vigorous, but compact growth when propagated both as a budded rose and on its own roots;

3. Disease resistance.

This combination of qualities is not present in previously available commercial cultivars of this type and distinguish 'POULbambe' from all other varieties of which we are aware.

As part of their rose development program, L. Pernille Olesen and Mogens N. Olesen germinated the seeds from the aforementioned hybridization during winter 1993 and conducted evaluations on the resulting seedlings in a controlled environment in Fredensborg, Denmark.

'POULbambe' was selected in the spring of 1994 by the inventors as a single plant from the progeny of the aforementioned hybridization.

Asexual reproduction of 'POULbambe' by traditional budding and rooted cuttings was first done by L. Pernille and Mogens N. Olesen in their nursery in Fredensborg, Denmark in summer 1994. This initial and other subsequent asexual propagations conducted in controlled environments have demonstrated that the characteristics of 'POULbambe' are true to type and are transmitted from one generation to the next.

BRIEF DESCRIPTION OF THE DRAWING

The accompanying color illustration shows as true as is reasonably possible to obtain in color photographs of this type the variety rose 'POULbambe'. Specifically illustrated in SHEET 1 are 'POULbambe's' foliage, flower buds, partially opened buds, and open blooms.

DETAILED DESCRIPTION OF THE VARIETY

The following is a description of 'POULbambe', as observed in its growth in a nursery in Jackson County, Oreg., on plants aged one year. Color references are made using The Royal Horticultural Society (London, England) Colour Chart, 1995, except where common terms of color are used.

For a comparison, several physical characteristics of the rose variety 'POULtrav', a rose variety from the same inventors described and illustrated in U.S. Plant patent application Ser. No. 09/277,240, dated Mar. 26, 1999 are compared to 'POULbambe' in Chart 1.

CHART 1

| | 'POULbambe' | 'POULtrav' |
|---|---|---|
| Color of open flower, outer side, middle zone. | Yellow-Orange Group 23D. | Yellow-Orange Group 14C to 23B |
| Petalage | 18–22 | 38–44 |
| Upon opening, color basal petal spot, outer side | Yellow Group 6B | Green-Yellow Group 1B |

Parents:
*Seed parent.*—'POULtrav'.
*Pollen parent.*—'POULurt'.

FLOWER AND FLOWER BUD

Blooming habit: Continuous.
Flower bud:
*Bud form.*—Ovate.
*Color.*—As sepals unfold, Yellow-Orange Group 20B.
*Sepals.*—Size: 35 mm long and 12 mm wide. Appendages: Weak appendages. Texture: Moderately pubescent. Color: Upper surface is Yellow-Green Group 146A in marginal zone and Yellow-Green Group 146D in middle and basal zones. Lower surface is Yellow-Green Group 144A in marginal zone and Yellow-Green Group 144C in middle and basal zones.
*Receptacle.*—Size: Small.
*Peduncle.*—Surface: Fine, white hairs present, with occasional stipitate glands. Color: Yellow-Green Group 146C. Strength: Strong. Length: 8 to 10 cm.
*Borne.*—Dense tops with 5 to 15 flowers per stem.
Flower bloom:
*Fragrance.*—Slight scent of honey.
*Size.*—Small to medium. Average flower diameter is 60 mm when open.
*Form.*—Shape of flower when viewed from the side: Upper part: Flattened convex. Lower part: Flattened convex. Viewed from above: Irregularly rounded.
*Petalage.*—Semi-double. Average range: 18–22 petals under normal conditions.
Color:
*Petals.*—Inner Side: Middle zone: Yellow-Orange Group 19B. Marginal zone: Yellow-Orange Group 19B. Basal petal spot: Yellow Group 6A. Outer side: Middle zone: Yellow-Orange Group 23D. Marginal zone: Yellow-Orange Group 23D. Basal petal spot: Yellow Group 6B.
*General tonality.*—On open flower Yellow-Orange Group 19A.
Petals:
*Petal reflex.*—Slight.
*Undulation of margin.*—Weak.
*Size.*—Small to medium.
*Shape.*—Obovate. Petal apex is rounded. Petal base is acute.
*Surface texture.*—Velvety.
*Duration.*—7 to 10 days.
*Persistence.*—Petals fall cleanly from the stem.
*Petaloids.*—Quantity: 1 to 2. Size: 15 mm (l)×10 mm (w). Color: Yellow-Orange Group 21A.
Reproductive organs:
*Anthers.*—Size: 1 to 2 mm long. Quantity: 50 to 60. Color: Yellow-Orange Group 22A.
*Filaments.*—Color: Yellow Group 12A.
*Stigmas.*—Position: Slightly superior ro anthers. Color: Yellow-Green Group 150C.
*Pistils.*—Size: 10 mm long. Quantity: 25 to 30.
*Filaments.*—Color: Yellow Group 12A.
*Styles.*—Color: Yellow-Green Group 150C.
*Hips.*—None observed.
*Pollen.*—None observed.

PLANT

Plant growth: Dense, compact, bushy well-branched, and even growth. When grown as a budded field grown plant on *Rosa multiflora* understock, the average height of the plant is 60 cm and the average width is 60 cm.
Stems:
*Thorns.*—Incidence: 6 to 8 per 10 cm of stem. Size: 4 to 7 mm. Shape: Deeply concave. Color: Greyed-Yellow Group 160B.
*Color.*—Young wood: Yellow-Green Group 144B. Older wood: Yellow-Green Group 144A and B.
*Texture.*—Young wood: Smooth. Older wood: Smooth.
Plant foliage:
*Leaf size.*—120 mm (l)×85 mm (w).
*Glossy.*—Upper side weak to medium glossiness.
*Color, mature foliage.*—Upper Leaf Surface: Green Group 137A. Lower Leaf Surface: Green Group 137C.
*Color, juvenile foliage.*—Upper Leaf Surface: Yellow-Green Group 144A. Lower Leaf Surface: Yellow-Green Group 144B.
*Anthocyanin intonation.*—Color: Greyed-Purple Group 184A.
Plant leaflets:
*Stipules.*—Size: 15 to 20 mm long. Color: Margins are Yellow-Green Group 146A; interior is Yellow-Green Group 144D. Stipitate Glands: Present on stipule margins. Anthocyanin: Greyed-Purple Group 184A.
*Petiole.*—Length: 2 to 5 mm (l). Color: Yellow-Green Group 144B. Underside: With sparse, fine white hairs. Anthocyanin: Greyed-Purple Group 184A Margins: With stipitate glands.
*Rachis.*—Color: Yellow-Green Group 144A. Underside: Occasional small thorn present. With fine, white hairs. Margins: With stipitate glands. Anthocyanin: Greyed-Purple Group 184A.
*Leaflet.*—Cross Section: Slightly concave. Margin Undulation: Weak. Shape: Ovate. Apex is acute, base is rounded.
*Terminal leaflet.*—Size: 75 mm (l)×35 to 40 mm (w). Shape: Ovate.
Disease resistance: Above average resistance to mildew, rust, black spot, and Botrytis under normal growing conditions in Fredensborg, Denmark and Hannover, Germany.
Cold hardiness: The variety 'POULbambe' has been found to be cold hardy in Fredensborg, Denmark and Hannover, Germany.

We claim:

1. A new and distinct variety of rose plant of the shrub rose class, substantially as herein illustrated and described as a distinct and novel rose variety due to its abundant amber-yellow flowers, disease resistance, and extended period of bloom.

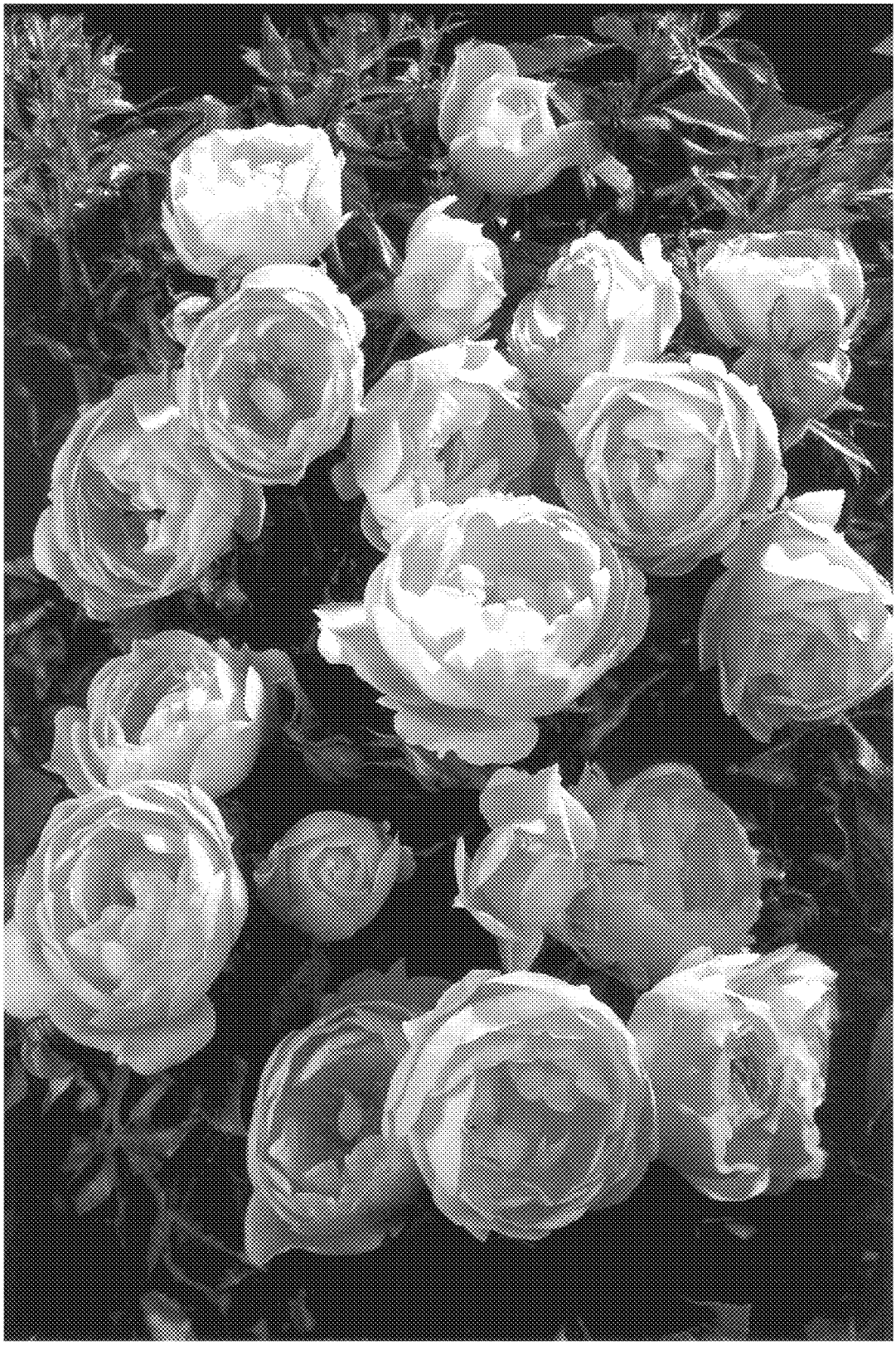

* * * * *